US012678337B2

(12) United States Patent
Rikihisa

(10) Patent No.: US 12,678,337 B2
(45) Date of Patent: Jul. 14, 2026

(54) TAPE PRODUCT

(71) Applicant: Hiroaki Rikihisa, Yokohama (JP)

(72) Inventor: Hiroaki Rikihisa, Yokohama (JP)

( * ) Notice: Subject to any disclaimer, the term of this patent is extended or adjusted under 35 U.S.C. 154(b) by 148 days.

(21) Appl. No.: 18/740,340

(22) Filed: Jun. 11, 2024

(65) Prior Publication Data

US 2024/0325205 A1 Oct. 3, 2024

Related U.S. Application Data

(62) Division of application No. 16/462,481, filed as application No. PCT/JP2017/041439 on Nov. 17, 2017, now abandoned.

(30) Foreign Application Priority Data

Nov. 24, 2016 (JP) ................................. 2016-227549

(51) Int. Cl.
 *A61F 13/00* (2024.01)
 *A61F 13/02* (2006.01)
(52) U.S. Cl.
 CPC .... *A61F 13/02* (2013.01); *A61F 2013/00663* (2013.01); *A61F 2013/00668* (2013.01); *A61F 2013/00702* (2013.01)
(58) Field of Classification Search
 None
 See application file for complete search history.

(56) References Cited

U.S. PATENT DOCUMENTS

| | | | |
|---|---|---|---|
| 10,332,775 B2 * | 6/2019 | Rusli ..................... H01L 21/486 |
| 2006/0195054 A1 * | 8/2006 | Smith ................... A61F 13/023 |
| | | | 602/42 |
| 2011/0070391 A1 | 3/2011 | Cotton |
| 2014/0142526 A1 | 5/2014 | Auguste et al. |
| 2015/0144259 A1 | 5/2015 | Laulicht et al. |
| 2015/0320605 A1 | 11/2015 | Pigg et al. |
| 2016/0089145 A1 | 3/2016 | Quintero et al. |
| 2016/0128873 A1 | 5/2016 | Martin et al. |
| 2016/0249924 A1 * | 9/2016 | Belson ............... A61B 17/0466 |
| | | | 606/216 |
| 2019/0038473 A1 | 2/2019 | Luckemeyer et al. |

FOREIGN PATENT DOCUMENTS

| | | | | |
|---|---|---|---|---|
| CN | 202498345 U | * | 10/2012 |
| JP | H05-146466 A | | 6/1993 |
| JP | H10-23923 A | | 1/1998 |
| JP | H10328268 A | * | 12/1998 |
| JP | 2000-189453 A | | 7/2000 |

(Continued)

OTHER PUBLICATIONS

JP 10328268 A Translation (Year 1998) (Year: 1998).*

(Continued)

*Primary Examiner* — Kim M Lewis
(74) *Attorney, Agent, or Firm* — ArentFox Schiff LLP

(57) ABSTRACT

The tape product prevents wounds on skin when peeling off a tape member from occurring. The tape product 100 includes a tape member 10 having an adhesive surface, and a mesh member 20 releasably provided on the adhesive surface of the tape member 10. When the tape product 100 is applied to skin, the adhesive surface of the tape member 10 adheres to the skin through the openings 21 of the mesh member 20.

5 Claims, 9 Drawing Sheets

(56) References Cited

FOREIGN PATENT DOCUMENTS

JP          2001-17463  A        1/2001
JP          2003319968  A   *  11/2003

OTHER PUBLICATIONS

JP 2003319968 A Translation (Year 2003) (Year: 2003).*
CN 202497345 U Translation (Year 2012) (Year: 2012).*
English Translation of JPH10328268A (Year: 2022).
International Search Report of corresponding International Application No. PCT/JP2017/041439, dated Jan. 30, 2018.
Laulicht, B., et al., "Quick-release medical tape", PNAS, vol. 109, No. 46, pp. 18803-18808, Nov. 13, 2012.

* cited by examiner

TAPE PRODUCT

CROSS REFERENCE TO RELATED APPLICATIONS

This application is a Divisional Application of U.S. patent application Ser. No. 16/462,481, filed Oct. 11, 2019, which is a National Stage Entry of International Application No. PCT/JP2017/041439, filed Nov. 17, 20217, which claims priority to Japanese Patent Application No. 2016-227549, filed Nov. 24, 2016. The disclosures of priority applications are hereby incorporated in their entirety by reference.

TECHNICAL FIELD

The present invention relates to a tape product such as those used for medical purposes.

BACKGROUND ART

In recent years, in the medical field, the condition of the skin is being managed more strictly than before, and there has been a demand to avoid skin wounds. For example, there is a need to prevent pressure tears that occur on pressed skin and skin tears that occur in patients with weak skin such as the elderly and infants.

First, medical equipment compression wounds (medical device related pressure ulcers) are a problem. With respect to this, according to the Japanese Society of Pressure Ulcers, in addition to commonly used medical devices, devices including nursing support equipment such as restraint bands are defined as "medical devices". Also, a wound generated by a local external force applied to the patient's body at the time of wearing the medical related device is referred to as a "medical device related pressure ulcer".

Second, skin tears (Skin Tear: Skin Lacerations) are also a problem. With respect to this, the Japanese Society of Wound, Ostomy, and Continence Management defines a skin tear as damage up to the deep dermis (partial wound) caused by tearing of the skin due to rubbing and slipping. Moreover, the tearing of the skin when removing a bandage is given as a specific example of a skin tear.

Such medical device related pressure ulcers and skin tears are more likely to occur in patients with skin problems such as patients with skin diseases, infants, and the elderly. In addition, these pressure ulcers and skin tears are particularly likely to occur when a highly adhesive skin adhesive tape is used. For example, consider cases in which tape is affixed to the skin of a patient with weak skin such as with ventilator tracheal tubes, indwelling vascular catheters, urethral catheters, nasogastric tubes, or transnasal oxygen cannulas. When securing a catheter or tube to a patient with a skin adhesive tape, a relatively adhesive skin adhesive tape is selected so that the tape does not come off. On the other hand, catheters for indwelling urethral catheters, nasogastric tubes, and transnasal oxygen cannulas need to be replaced regularly in order to be cleaned. In other words, peeling off the adhesive tape from the patient's skin is necessary. However, when removing the adhesive tape, the adhesive tape exerts a strong force on the skin of the patient. Then, when the skin of the patient is weak, when the adhesive tape is peeled off, a wound may be generated at the site to which a strong force is applied. Furthermore, if the medical tube is repeatedly replaced, a strong force is applied to the same area of the skin. As a result, there is the problem that a wound that has occurred once can then become worse.

Therefore, in order to avoid this problem, the solution devised is to put the tape on another area.

PRIOR ART DOCUMENT

Non-Patent Documents

Non-Patent Document 1: Bryan Laulicht, Robert Langer, and Jeffrey M. Karp, "Quick-Release Medical Tape", PNAS, Vol. 109, No. 46, 18803-18808 (2012)

DISCLOSURE OF INVENTION

Summary of the Invention

Conventionally, in order to reduce the wound that occurs at the time of exfoliation of the above-mentioned adhesive tape for skin, several approaches have been used. For example, to reduce the external force applied to the patient's skin when peeling off the adhesive tape, weakening the adhesive strength of the adhesive tape has been considered. For example, using an adhesive with low tackiness has been. Or, instead of applying the adhesive to the entire surface of the adhesive tape, applying the adhesive to a part of the adhesive tape, or by reducing the area of the adhesive by partially removing the adhesive from the adhesive applied to the entire side of the adhesive tape has been considered. However, for these methods, the adhesion to the skin decreases even when the adhesive tape for skin is not peeled off. Therefore, fixation for things such as medical tubes will be insufficient.

Also, as shown in Non-Patent Document 1, a for avoiding applying a strong force to the skin while maintaining the adhesion of the adhesive tape, a method in which an intermediate layer is provided between the adhesive layer of the adhesive tape and the base layer to facilitate the separation of the two is known. In this method, when the adhesive tape is peeled off, the adhesive layer and the base layer peel in the intermediate layer. Therefore, only the base layer can be removed while leaving the adhesive layer on the adhesive surface. Then, while maintaining the adhesive strength of the adhesive tape, avoiding applying a strong force to the object when peeling off the base layer becomes possible. The use of such an intermediate layer approach to medical tape reduces the risk of skin wounds occurring when the tape is removed when peeling off the tape. However, after removing the base layer, the adhesive layer remains on the skin. The adhesive layer left on the skin then is able to irritate the skin. Moreover, leaving the adhesive layer for a long time on the skin of a patient susceptible to irritation is not possible. For this reason, the adhesive layer also needs to be removed at an early stage from the patient's skin. Then, when peeling off the adhesive layer a strong force is applied to the skin. In the end, there is a risk of skin damage.

Also, a method (a remover method) in which a solvent is applied to an adhesive tape just before peeling off a bandage to weaken the adhesive force and then peeling off adhesive tape in order to reduce the occurrence of a wound is known. However, with such a remover method, the solvent remains on the skin after treatment. Then, if the adhesive tape is refixed in that state, there is a problem that the adhesive strength of the refixed adhesive tape falls. Furthermore, with the waterproof tape, the solvent does not get into the tape member, and there is a problem which takes time and effort in order to peel off the tape in that it is necessary to peel off the member a little and squeeze the solvent while directly impregnating it between the adhesive layer and the skin.

Furthermore, if conventional adhesive tapes are used to secure medical devices to the skin, sometimes the adhesive surface with the skin becomes large. Then, when peeling off such an adhesive tape, a large force was required. As a result, for work that requires precision and accuracy, peeling off the adhesive tape at the same time becomes difficult. Then, this causes the following problems.

For example, as for when a central venous catheter placed in a neck is fixed to the skin with and adhesive tape, consider a case where only the adhesive tape is replaced while the catheter remains placed in the neck. In this case, when replacing the adhesive tape, removing only the adhesive tape adhering to the skin without moving the position of the catheter as much as possible is necessary. In other words, the task of maintaining the position of the catheter with high accuracy is required such as with holding down the catheter with a finger so that the injection needle for infusion does not move. However, when peeling off the adhesive tape, a large force is applied to the skin. Therefore, maintaining the position of the catheter with high accuracy in such a state has been difficult.

Also, conventionally, in order to prevent the skin of the patient from being damaged at the time of peeling off the bandage, for example, the adhesiveness of the bandage is weakened to protect the stratum corneum of the skin so that peeling off of the stratum corneum does not occur when the bandage is peeled off has been considered. However, in order to firmly bond a weak adhesive bandage to the skin, expanding the area being stuck to the skin is necessary. However, increasing the application area of the bandage increases the possibility that the bandage will be applied to a portion where the cutaneous layer (skin) and subcutaneous tissue (hypodermis) are weakly connected, or to a portion originally having a wound on the epidermis. Then, when the bandage is peeled off, such portion is broken and the skin peels off from the subcutaneous tissue. In other words, the conventional (silicon-based) bandage with a weakened adhesiveness in order to protect the stratum corneum needs to have a large application area to strengthen the adhesiveness, and in this case, even if the patient's stratum corneum can be protected, there was also the problem that the skin cannot always be prevented from being damaged from peeling off from the subcutaneous tissue.

Therefore, according to the present invention, an object of the present invention is to make it easy to peel off the adhesive tape while maintaining the adhesion of the adhesive tape to the skin, and to prevent a wound from being generated on the skin when the adhesive tape is peeled off. More specifically, the present invention is aimed at preventing damage caused by skin peeling off from subcutaneous tissue.

After intensive investigation into solutions to the problems posed by the above-mentioned prior art, the inventors of the present invention found that wounds can be prevented from occurring in the peeled portion of a tape member by providing a mesh member on an adhesive side of a tape member, which during adhesion, the adhesive surface adheres to the skin of the patient through the openings of the mesh member, and during peeling, the tape member is peeled while holding the mesh member against the skin surface. Then, the present inventors considered that the problems of the prior art could be solved based on the above findings, and completed the present invention. Specifically, the present invention has the following configuration.

The present invention relates to a tape product 100 adhered to an object, such as a patient's skin. The tape product 100 of the present invention comprises a tape member 10 having an adhesive surface, and a mesh member 20 provided on the adhesive surface of the tape member 10 in a releasable manner. The tape product 100 is configured such that the adhesive surface of the tape member 10 adheres to the object through the openings 21 in the mesh member 20.

According to the above configuration, the adhesive surface of the tape member 10 adheres to the skin through the openings 21 in the mesh member 20 at the time of bonding, so that the adhesive strength of the entire tape product 100 can be maintained. On the other hand, at the time of exfoliation, while applying a force in the direction of pressing the mesh member 20 against the skin surface, the tape member 10 is pulled in the opposite direction. At this time, the pulling force of the tape member 10 is relaxed or offset by the pressing force of the mesh member 20. Thereby, when peeling the tape member 10, avoiding applying a large external force to the skin is possible. As a result, peeling off the tape member 10 becomes easy, and preventing a wound from being generated on the skin when the tape member 10 is peeled off is possible. Furthermore, even if the tape product 100 is attached to the surface of hairy skin, since the mesh member 20 acts to press down the hair, preventing the hair from coming off when the tape member 10 is peeled off is possible. As a result, the tape member 10 can be peeled off with little pain to the patient. In addition, according to the tape product of the present invention, sufficient adhesion can be obtained without covering a wide application area, so that preventing the skin from being peeled off from the subcutaneous tissue is possible.

In the present invention, the tape member 10 has a base layer 11 and an adhesive layer 12 laminated on the base layer 11 which constitutes an adhesive surface. In this case, the adhesive layer 12 is formed of a gel-like adhesive, and the gel-like adhesive layer 12 may be deformed and exuded from the openings 21 in the mesh member 20. "Gel" generally refers to dispersed materials that have high viscosity and lost flowability.

When the tape product 100 is pressure-bonded to the skin by making the adhesive layer 12 gel-like as in the above configuration, the gel adhesive layer 12 exudes from the gaps (openings 21) of the mesh member 20 and adheres to the skin. Thereby, the adhesiveness of the tape member 10 becomes large. Therefore, even if the mesh member 20 is interposed between the tape member 10 and the skin, the tape product 100 is able to maintain sufficient cohesion to secure medical tubing or needles.

In the present invention, the tape member 10 has a base layer 11 and an adhesive layer 12 laminated on the base layer 11 which constitutes an adhesive surface. In this case, the base layer 11 is formed of a stretchable material, and the base layer 11 may be extended so that the adhesive layer 12 adheres to the object through the openings 21 in the mesh member 20. Moreover, in this case, the adhesive layer 12 may be formed of a gel-like adhesive like that previously mentioned or may be formed of a non-gel-like adhesive. The adhesive layer 12 may be disposed on the entire surface of the base layer 11. Also, the adhesive layer 12 may be disposed on a portion of the base layer 11. In the case of arranging the adhesive layer 12 on a portion of the base layer 11, the adhesive layer 12 should be arranged at least on a portion corresponding to the openings 21.

As described above, the base layer 11 is formed of, for example, a stretchable material such as a non-woven fabric.

Then, when the tape product 100 is pressure-bonded to the skin, the stretchable base layer 11 stretches, and the stretchable adhesive layer 12 adheres to the skin through the openings 21 in the mesh member 20. Thereby, the adhesive force of the tape member 10 becomes large. Therefore, even if the mesh member 20 is interposed between the tape member 10 and the skin, the tape product 100 can be used to maintain sufficient cohesion to secure medical tubing or needles.

The tape product 100 of the present invention may further include a release layer 30 between the mesh member 20 and the adhesive layer 12 of the tape member 10. The release layer 30 is not present in the openings 21 in the mesh member 20. Therefore, even when the release layer 30 is interposed between the mesh member 20 and the tape member 10, the adhesive layer 12 of the tape member 10 adheres to an object through the openings 21 in the mesh member 20.

By providing the release layer 30 between the mesh member 20 and the tape member 10 as in the above configuration, the tape member 1 can be easily peeled off from the mesh member 20 while maintaining the adhesiveness of the tape member 10.

In the present invention, the tape member 10 may further have a grippable layer 13 laminated on the base layer 11. In this case, the grippable layer 13, the base layer 11, and the adhesive layer 12 are laminated in this order. The grippable layer 13 is formed so as to be thicker than at least the base layer 11. That is, the grippable layer 13 has such a thickness that it can be picked with fingertips. In particular, the grippable layer 13 is preferably formed of a material that is able to be elastically deformed by an external force in the thickness direction.

By providing the grippable layer 13 partially or entirely on the surface of the base layer 11 opposite the adhesive layer 12, as in the above configuration, pulling the tape member 10 in the peeling direction from the mesh member 20 becomes easy by holding the grippable layer 13. As a result, the tape member 10 can be easily peeled off from the mesh member 20 while maintaining the adhesiveness of the tape member 10.

In the present invention, the mesh member 20 may be provided on the overall adhesive surface of the tape member 10 and may have an extended portion 22 extending from the edge of the adhesive surface.

If the area of the mesh member 20 is completely the same as or smaller than the area of the tape member 10, then when peeling the tape member 10 from the mesh member 20, pressing the mesh member 20 to the skin surface side becomes difficult. On the other hand, like the above configuration, by the mesh member 20 having the extended portion 22 at least partially rendered from the adhesive surface edge of the tape member 10, peeling off the tape member 10 while holding the extended portion 22 with finger tips is possible. Thus, the tape member 10 can be easily peeled off from the mesh member 20 while maintaining the adhesiveness of the tape member 10. Moreover, a part of the tape member 10 may be separated by perforations and disposed on the extended portion 22.

In the present invention, the base layer 11 of the tape member 10 is formed of a stretchable material, and the stretching ratio of the tape member 10 may be higher than the stretching ratio of the mesh member 20. The "stretching ratio" is the ratio of the length in the extension direction in the maximum extension state to the length in the extension direction in the natural state.

As in the above configuration, by setting the stretching ratio of the mesh member 20 low or not at all, and making the stretching ratio of the tape member 10 higher than the mesh member 20, the tape member 10 is able to be easily peeled off from the mesh member 20.

The tape product 100 of the present invention may be provided with a plurality of tape members 10a, 10b . . . on a single mesh member 20. That is, slits may be formed in the tape member 10 disposed on the mesh member 20 and may be separated into two or more.

First, the first tape member 10a is peeled off by providing the plurality of tape members 10a, 10b . . . separately on the mesh member 20 as in the above configuration; after that, a peeling operation such as peeling the second tape member 10b is possible. Because partially removing the tape members is easier instead of peeling off all of the tape members at once, peeling off the tape members 10 without damaging the patient's skin becomes easier.

According to the tape product of the present invention, the tape members are easily peeled off from the skin while maintaining the adhesion of the tape members to the skin. Therefore, preventing the skin from being wounded when the tape members are peeled off is possible.

BRIEF DESCRIPTION OF THE DRAWINGS

FIG. 11 shows an example of a tape product of the type used for wrapping.

FIG. 12 shows an example of a T-shaped tape product for protecting a fingertip.

DETAILED DESCRIPTION OF THE INVENTION

Hereinafter, embodiments of the present invention will be described using the drawings. The present invention is not limited to the embodiments described below, and includes those appropriately modified by a person skilled in the art based on the present invention within the scope of obviousness. Moreover, in the present specification, "A~B" includes "A or more and B or less".

1. First Embodiment

A first embodiment of a tape product 100 according to the present invention will be described with reference to FIGS. 1 to 4. The tape product 100 according to the present invention can be used, for example, as a medical tape attached to the skin of a patient.

Figure 1:
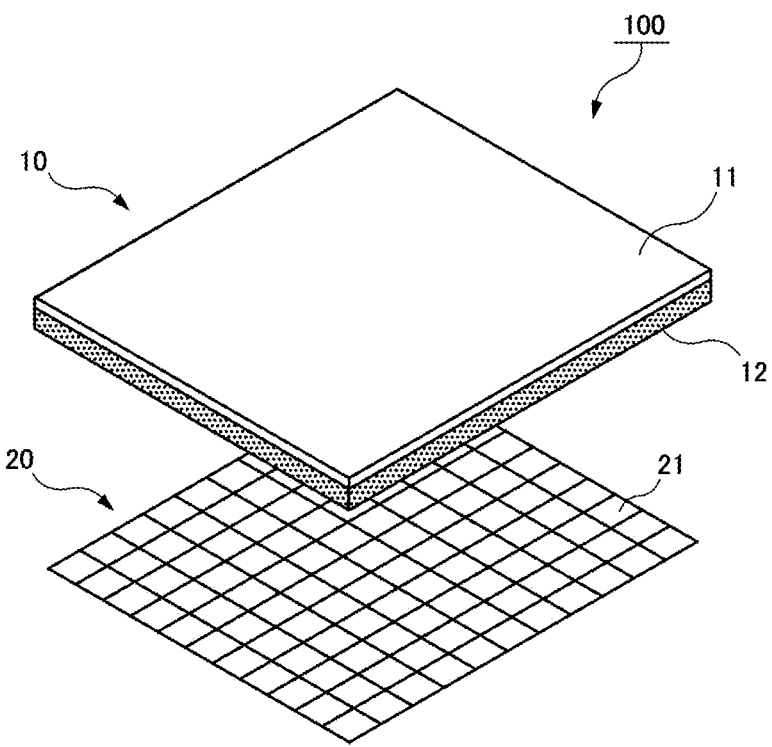
FIG. 1 is an exploded perspective view schematically showing a component of the tape product according to a first embodiment.

As shown in FIG. 1, the tape product 100 comprises a tape member 10 and a mesh member 20. The tape member 10 is a member having an adhesive surface on at least one side. The mesh member 20 is a mesh-like member having a plurality of openings 21. The mesh member 20 is attached to the adhesive surface of the tape member 10 and can be peeled off from the tape member 10 by hand. Preferably, the mesh member 20 is attached over substantially the entire adhesive surface of the tape member 10. As examples, the area in which the mesh member 20 is attached to the tape member 10 is preferably 80~100% or 90~100% of the area of the adhesive surface of the tape member 10, and also, the mesh member 20 may have a portion extending beyond the edge of the tape member 10.

The tape member 10 basically comprises a base layer 11 and an adhesive layer 12. The base layer 11 and the adhesive layer 12 are inseparably fixed. The adhesive layer 12 is laminated on one side of the base layer 11 to form a laminated structure, and the adhesive layer 12 forms an adhesive surface.

The base layer 11 may be formed of a material used as a base material for a general medical tape. For example, the base layer 11 can be formed of a stretchable woven or non-woven fabric, a soft film, or the like. Specifically, various materials such as polyvinyl chloride film, polyethylene film, polyester film, polypropylene film, ethylene-propylene copolymer film, ethylene-vinyl acetate copolymer film can be used as the base layer 11.

The adhesive layer 12 is a layer that adheres to the skin, and basically contains an adhesive polymer as a main component. Examples of the material of the adhesive constituting the adhesive layer 12 include, for example, synthetic rubber-based adhesives based on styrene-isobutylene-styrene copolymers as a main component, polyurethane adhesives, polysiloxane adhesives, natural rubber adhesives, polyether adhesives, and acrylic adhesives, which can be used alone or in combination of two or more. Also, the state of the adhesive constituting the adhesive layer 12 is a gel-like type in which the dispersion substance has high viscosity and lost flowability besides those with high viscosity in a liquid state.

Figure 2:
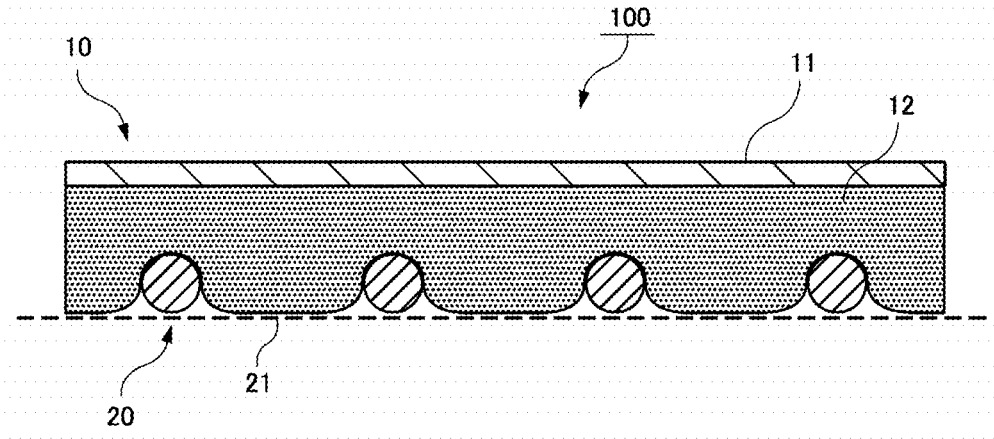
FIG. 2 is a cross-sectional view in the thickness direction schematically showing the tape product according to the first embodiment.

Here, FIG. 2 is a cross-sectional view in the thickness direction showing an example where the adhesive layer 12 is formed of a gel-like adhesive. As shown in FIG. 2, if the adhesive layer 12 is made of a deformable gel adhesive, when the tape product 100 is pressed against the skin of a patient, the adhesive layer 12 exudes from the openings 21 of the mesh member 20 and adheres to the skin surface. "Gel" generally refers to dispersed materials that have high viscosity and lost flowability. In particular, in the present specification, "gel" means a dispersion based material containing water, silicone oil or the like as a dispersion medium and a polymer in the form of a three-dimensional network as a dispersoid. That is, the "gel" in the present invention has flexibility which can be deformed while losing flowability by containing the dispersion medium in the network structure of the polymer which is one of the dispersoids.

Such gel-like adhesive layer 12, for example, may be a known adhesive used in adhesive patches such as a poultices. As examples, rubber-based adhesives with a main component being natural rubbers, silicone-based adhesives (silicone gel) with a main component being polydimethylsiloxane rubbers, acrylic adhesives with a main component being n-butyl acrylates, urethane-based adhesives, glycol-based polyethylene adhesives, and polyvinyl alcohol-based adhesives can be suitably used for the adhesive layer 12. In particular, adhesives for medical use are preferable. The thickness of the gel-like adhesive layer 12 is not particularly limited, but may be, as examples, about 0.2~2.0 mm or 0.5~1.5 mm, and preferably, the thickness is larger than the thickness of the mesh member 20.

Figure 3:
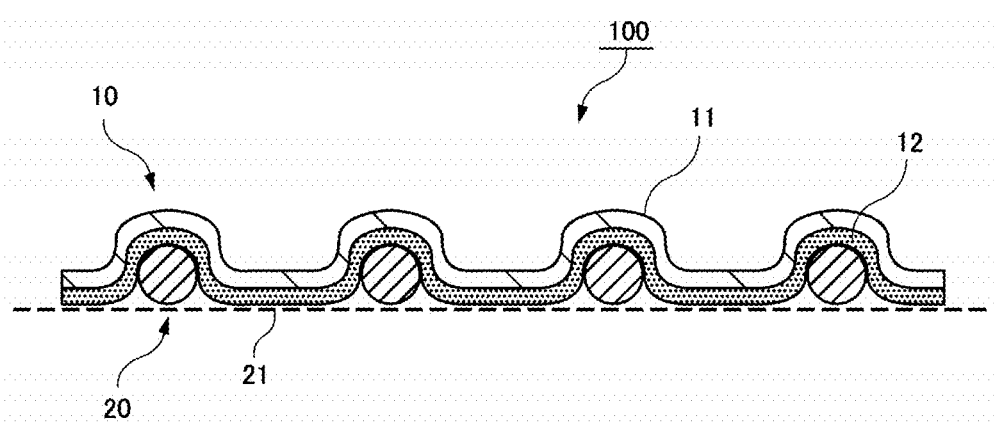
FIG. 3 is a cross-sectional view in the thickness direction schematically showing a modified example of the tape product according to the first embodiment.

On the other hand, the cross-sectional view in the thickness direction shown in FIG. 3 shows an example in which the adhesive layer 12 is formed of a non-gel adhesive. As shown in FIG. 3, even if the adhesive layer 12 is not a gel type, there is no problem as long as the base layer 11 laminated thereon is stretchable. In this case, when the tape product 100 is pressed against the skin of a patient, as the base layer 11 stretches, the adhesive layer 12 adheres to the skin through the openings 21 in the mesh member 20. Thus, the adhesion of the tape product 100 can be maintained also by forming the base layer 11 with a stretchable material. Examples of stretchable materials are woven, non-woven or porous films. Also, for example, fibers made of thermoplastic resin such as polypropylene, polyethylene, polyester and nylon may be subjected to a hydrophilization treatment to be further made into a non-woven fabric. Examples of the non-woven fabric include air through non-woven fabric, point-bonded non-woven fabric, spun-bonded non-woven fabric, and melt-blown non-woven fabric.

If the base layer 11 is formed of a stretchable material, the stretching ratio of the tape member 10 provided with the stretchable material is, as examples, preferably 110% or more or 150% or more, and more preferably 110 to 300% or 150 to 250%. Here, "stretching ratio" is the ratio (percentage) of the length in the stretching direction in the maximum stretching state to the length in the stretching direction in the natural state. In the present invention, the stretching ratio is measured, for example, as follows. First, the object to be measured is left for 60 minutes in an atmosphere of relative humidity 60%±5% RH at 10° C.±2° C., and the length (A) in the direction of elongation in this natural state is measured. Second, the object measured in the natural state is stretched to a state just before breaking in the extension direction (that is, the maximum extension state), and the length (B) in the stretching direction in the maximum extension state is measured. Then, (B/A)×100 is calculated to obtain the stretching ratio.

The mesh member 20 is a member having a mesh structure in which a plurality of openings 21 are defined by interlacing yarns or fibers. Alternatively, it may also be a member formed by molding plastic or the like into a grid shape. In the present invention, the mesh member 20 is arranged so as to adhere to the adhesive layer 12 of the tape member 10. With respect to the mesh member 20, the adhesive layer 12 of the tape member 10 is able to be attached to an object such as skin through the openings 21 in the mesh member 20. If a thing is able to satisfy such conditions, the material and structure of the mesh member 20 may be known ones and are not particularly limited. For example, the mesh member 20 may be one in which one or two or more types of thread or fibrous material such as nylon, polyester, saran, polyethylene, polypropylene, polyvinylchloride, ethylene-ethyl acrylate copolymer, polytetrafluoroethylene, surlyn, or metal foil are woven into a mesh shape. Alternatively, it may be formed in a grid shape.

Also, the mesh member 20 is configured so as to be peelable from the adhesive surface (adhesive layer 12) of the tape member 10. The mesh member 20 may be one that is able to be peeled off the adhesive surface of the tape member 10 by hand without causing breakage or tearing in both the mesh member 20 and the tape member 10. As an example, the peel strength of a 24 mm wide mesh member 20 from a 24 mm wide tape member 10 is preferably less than 15000 mN/20 mm, and more preferably 7500 mN/20 mm or less, and even more preferably 1500 mN/20 mm or less. As an example, it is desirable that the peel strength be the same as or less than the 3M™ Multipore™ Highly Breathable Water Repellent Tape EX Elastic Cotton Cloth (Light Brown) 25 4733EP-25 which is sold by 3M as a "firmly fixed type" when peeling off the mesh member after attaching it. The lower limit of the peel strength is not particularly limited as long as the mesh member 20 is adhered to the tape member 10. The lower limit value of the peel strength may be, as examples, 20 mN/20 mm or more, or 50 mN/20 mm or more. As an example, it is desirable that the peel strength be the same as or greater than the 3M™ Gentle Peel Off Silicone Non-Woven Tape (Light Blue) 19 2775EP-0 which is sold by 3M as a "skin-friendly hypoallergenic type" when peeling off the mesh member after attaching it. Here, the term "peel strength" as used herein means that a mesh member is held between the tape member and the release paper, and the mesh member is attached to the adhesive surface of the tape member using a 2 kg roller, then 30 minutes thereafter, after removing the release paper, the peel strength is measured as the adhesive strength in a tape peel test under the conditions of a peel angle of 180° and a peel speed of 0.3 m/min.

In addition, the areas of the openings 21 in the mesh member 20 are preferably 4 mm² or more, and can be 4~40 mm², 5~35 mm², or 6~30 mm². Note that if there are a plurality of openings 21 with different areas, the average size of the areas of the openings present in a certain range (for example, a range of a 20 mm×20 mm square) may be within the range of the values described above. Thus, by keeping the openings 21 in the mesh member 20 in the range of 4~40 mm², the adhesiveness of the tape member 10 is maintained, and when the tape member 10 is peeled from skin, wounds can be effectively prevented from developing. Also, the mesh member 20 preferably has openings covering about 20~80% or about 30~60%. Further, the shape of the openings 21 in the mesh member 20 may be triangular, square, pentagonal, hexagonal, or some other polygonal shape. Additionally, the mesh member 20 may be formed by combining a plurality of these types of polygonal openings 21. Also, the thickness of the mesh member 20 is not particularly limited, but is preferably 0.01 mm to 1.0 mm. In order not to leave marks on the skin, the thickness of the mesh member 20 is preferably 0.01 mm to 0.1 mm.

In the present invention, the stretching ratio of the mesh member 20 is preferably lower than the stretching ratio of the tape member 10 described above. As an example, the stretching ratio of the mesh member 20 is preferably in the range of 100~200%, which is lower than the stretching ratio of the tape member 10. As a further example, when the stretching ratio of the mesh member 20 is 100%, the stretching ratio of the tape member 10 is preferably 110~300% or 150~250%. As described above, by setting the stretching ratio of the mesh member 20 lower than that of the tape member 10, the tape member 10 can be easily peeled off from the mesh member 20.

The strength of the tape product of the present invention including the mesh member and the tape member described above when applied to the skin and peeled off is desirably similar to existing tape products. As an example, it is desirable that the strength is equal to or less than that as with the case where the 3M™ Multipore™ Highly Breathable Water Repellent Tape EX Elastic Cotton Cloth (Light Brown) 25 4733EP-25 which is sold by 3M as a "firmly fixed type" is attached to the skin and removed. More preferably, it is desirable that the strength is equal to or more than that as with the case of attaching the mesh member to the skin by the 3M™ Gentle Peel Off Silicone Non-Woven Tape (Light Blue) 19 2775EP-0 which is sold by 3M as a "skin-friendly hypoallergenic type" and then peeling it off. Also, as for the strength when the tape product of the present invention is measured partially in accordance with JIS Z 0237 (2009) "Adhesive tape, adhesive sheet test method (10.4 measurement of peeling strength)", the strength when a tape product of the present invention having a width of 24 mm is attached to and peeled from a SUS 304 steel plate "surface finish BA (after cold rolling, bright heat treatment, surface roughness specified in JIS B 0601)" of 24 mm in width is preferably less than 15000 mN/20 mm, is more preferably 7500 mN/20 mm or less, and even more preferably 1500 mN/20 mm or less. The lower limit value of the peel strength may be, as examples, 20 mN/20 mm or more, or 50 mN/20 mm or more.

Figure 4:
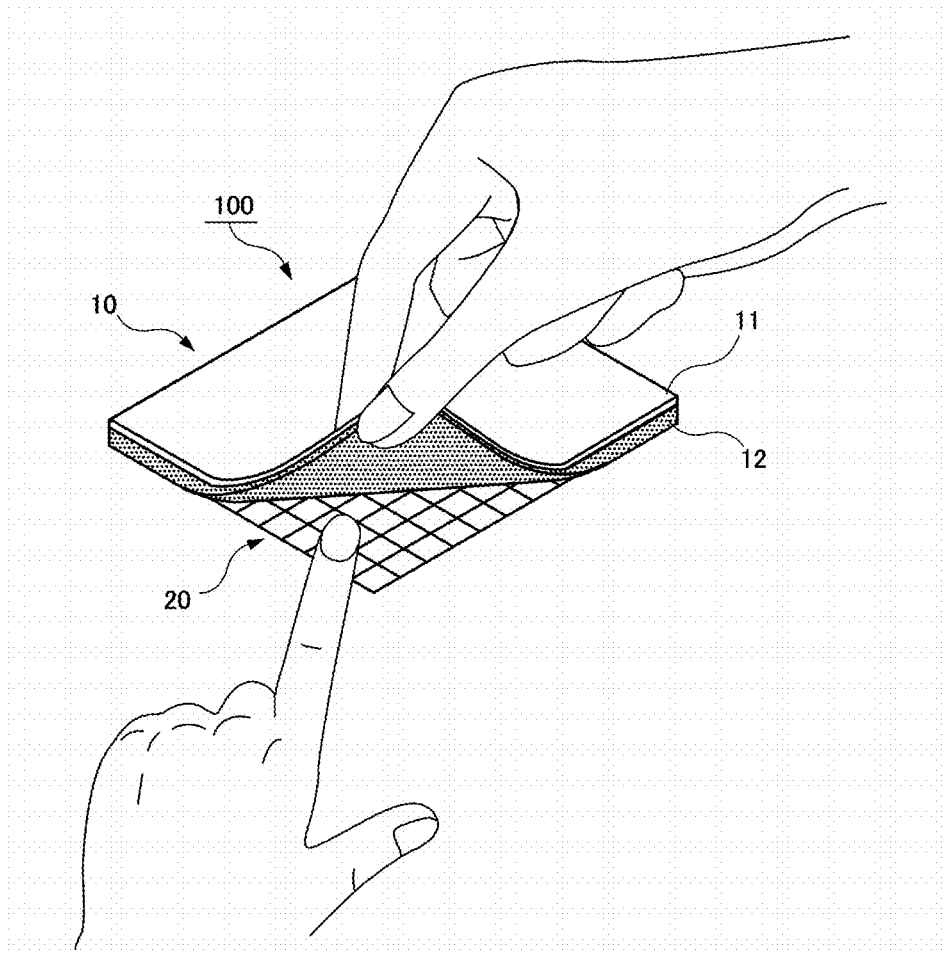
FIG. 4 is a perspective view showing an example of an operation for peeling the tape product from the skin.

FIG. 4 shows an example of how to use the tape product 100 provided with the tape member 10 and the mesh member 20 described above. As shown in FIG. 4, with the mesh member 20 attached to the adhesive surface of the tape member 10, the tape product 100 is attached to the skin or the like of the subject patient. Then, when removing the tape product 100 from the skin surface, the tape member 10 is first peeled off from the mesh member 20. For this example, a user holds the tape member 10 with one hand, and the mesh member 20 may be pressed against the skin with the other hand. As a result, the tape member 10 can be peeled from the skin without the adhesive surface of the tape member 10 pulling on hair growing on the skin surface or damaging the skin of the patient. In addition, since mesh member 20 itself does not have adhesive force, after removing the tape member 10, the mesh member 20 can be easily removed. Therefore, the tape member 10 can be easily peeled while maintaining the adhesion of the tape member 10 to the skin, and preventing a wound from being generated on the skin when the tape member 10 is peeled off is possible. Also, by holding down the hair on the skin surface with the mesh member 20, because the hair can be prevented from being caught in the tape member 10, the tape member 10 can be peeled off with almost no pain.

Also, if the adhesive strength of the adhesive layer 12 is insufficient, a medical adhesive or adhesive agent may be further applied to the surface of the tape product 100 (that is, on the mesh member 20). The adhesive used here is one that is viscous and able to be re-adhered, but on the other hand, the adhesive is one which solidifies and adheres to an object when exposed to air. With respect to the medical adhesives and adhesive agents, generally available ones can be appropriately adopted. Although a medical adhesive or adhesive may be applied to the surface of the tape product 100 (that is, on the mesh member 20) in advance, it may be applied when the tape product 100 is attached to the skin. In the former case, the tape product may be stored in a sealed container or bag to prevent drying. As such a bag, using known bags containing a patch such as poultice is possible. Also, a bag in which a plastic film and a metal foil are combined in multiple layers can be used.

2. Second Embodiment

Subsequently, a second embodiment of the tape product 100 according to the present invention will be described with reference to FIGS. 5 and 6. For the embodiment described below, descriptions of the same configurations as those of the first embodiment described above will be omitted, and descriptions will focus on those configurations different from the first embodiment.

Figure 5:
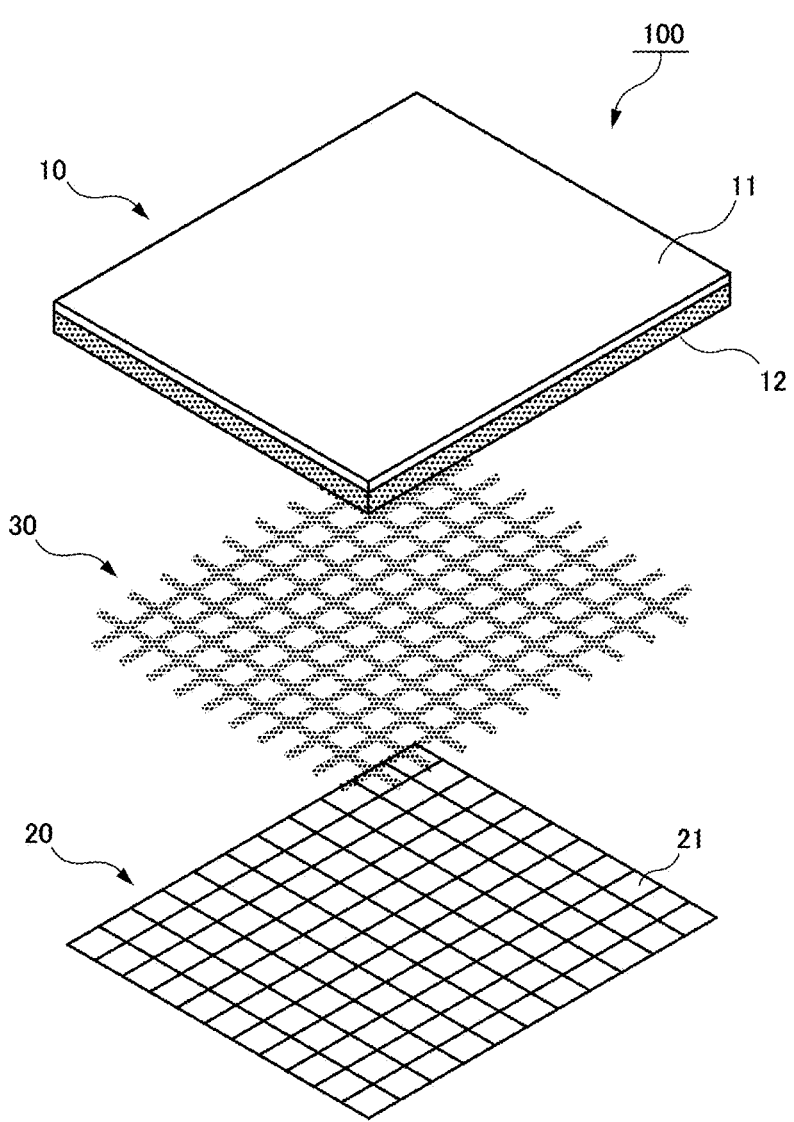
FIG. 5 is an exploded perspective view schematically showing components of the tape product according to a second embodiment.
Figure 6:
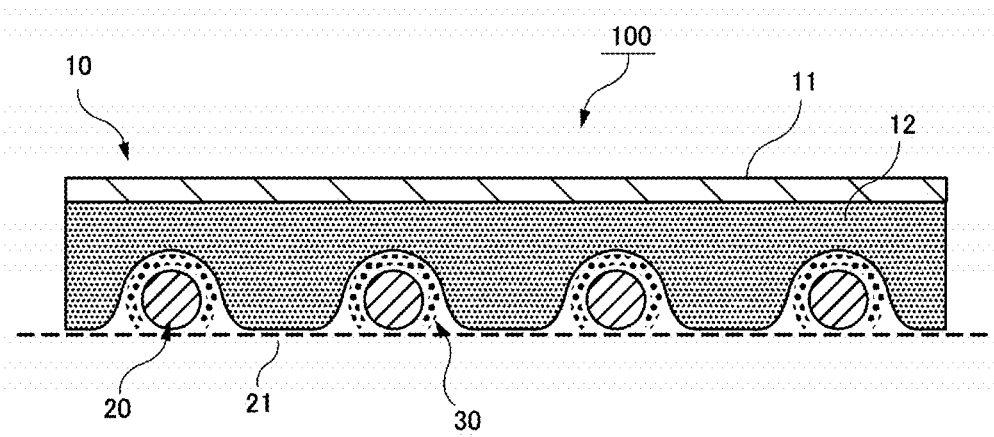
FIG. 6 is a sectional view in the thickness direction schematically showing a tape product according to the second embodiment.

As shown in FIGS. 5 and 6, the tape product 100 according to the second embodiment further includes a release layer 30 between the tape member 10 and the mesh member 20. The release layer 30 is provided for the purpose of facilitating peeling of the tape member 10 from the mesh member 20. Because the tape product 100 of the present invention is assumed to be used as a medical tape as one example, the release layer 30 is preferably made of, for example, a powder such as baby powder, which is used in medical applications. However, the release layer 30 is not limited to this, and may be formed, for example, by coating the surface of the mesh member 20 with a known release agent.

Further, the release layer 30 is provided only between the thread-like or fibrous material constituting the mesh member 20 or the plastic formed in a lattice shape and the adhesive surface of the tape member 10, and is not present in the portions corresponding to the openings 21 in the mesh member 20. Therefore, even if the release layer 30 is interposed between the two, the adhesive surface of the tape member 10 adheres to the skin through the openings 21 in the mesh member 20 as with the first embodiment, and at that time, no releasing agent gets between the adhesive surface and the skin. Thereby, the tape member 10 can be easily peeled off from the mesh member 20 while maintaining the adhesive force of the tape member 10. As an example, before attaching the mesh member 20 to the adhesive surface of the tape member 10, baby powder or the like is sprinkled on the mesh member 20 itself. Then, the surface of the mesh member 20 onto which the baby powder is deposited is attached to the adhesive surface of the tape member 10. As a result, the release layer 30 is formed only between the threads or fibers forming the mesh member 20 or the plastic formed in a lattice shape and the adhesive surface of the tape member 10.

3. Third Embodiment

Figure 7:
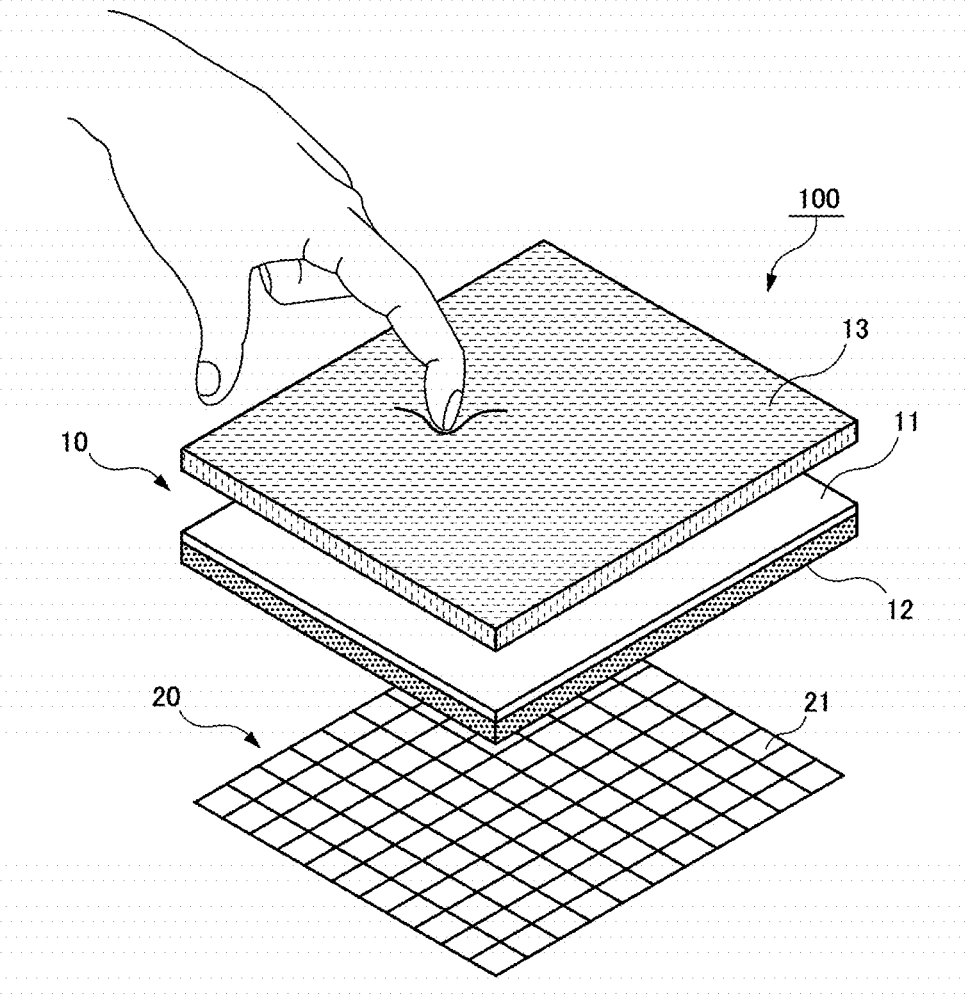
FIG. 7 is an exploded perspective view schematically showing components of a tape product according to a third embodiment.

Subsequently, FIG. 7 shows a third embodiment of the tape product 100 according to the present invention. As shown in FIG. 7, in the tape product 100 according to the third embodiment, the tape member 10 further includes a grippable layer 13 in addition to the configuration of the first embodiment described above. The grippable layer 13 is laminated on the surface of the base layer 11 opposite to the surface on which the adhesive layer 12 is present and is fixed to the base layer 11 in a non-releasable manner. For this reason, this tape member 10 has a structure in which the adhesive layer 12, the base layer 11 and the grippable layer 13 are laminated in this order of distance starting from the skin.

The grippable layer 13 is for making it easy to grasp the tape member 10 when the tape member 10 is peeled off from the mesh member 20. That is, if the mesh member 20 is stacked in substantially the same area as the tape member 10 or when the mesh member 20 is smaller than the tape member 10, peeling off the tape member 10 from the mesh member 20 becomes difficult, but such a problem can be solved by providing the grippable layer 13 on the top layer of the tape member 10. As shown in FIG. 7, the grippable layer 13 is preferably formed thicker than the base layer 11 and formed of a material that can be elastically deformed in the thickness direction. The material for forming the grippable layer 13 is not particularly limited. For example, the grippable layer 13, may be a sponge or silicone rubber. In particular, with respect to ease of manually grasping, the grippable layer 13 is preferably formed of a sponge. For the sponge, a known urethane sponge or a foamed rubber sponge can be adopted. The thickness of the grippable layer 13 is preferably such that it can be grasped by fingertips, and for example, is preferably set to 1~10 mm or 2~5 mm.

4. Fourth Embodiment

Figure 8:
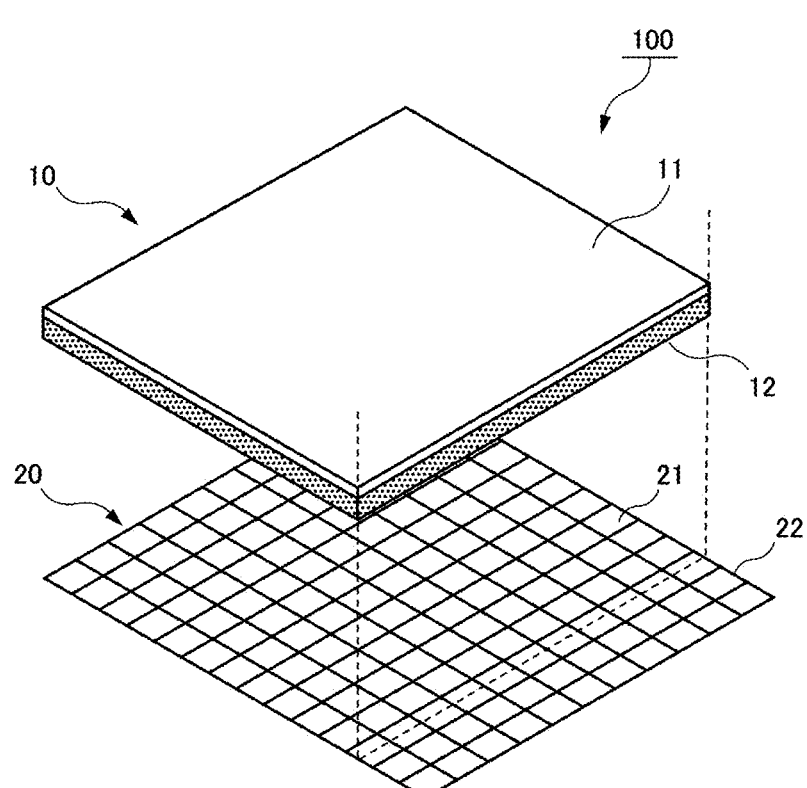
FIG. 8 is an exploded perspective view schematically showing components of a tape product according to a fourth embodiment.

Next, FIG. 8 shows a fourth embodiment of the tape product 100 according to the present invention. As shown in FIG. 8, in the fourth embodiment, the mesh member 20 has an extended portion 22 extending from the edge of the tape member 10. That is, while the mesh member 20 is preferably provided so as to basically cover the overall adhesive surface of the tape member 10, in the fourth embodiment, the mesh member 20 has an extended portion 22 protruding beyond the adhesive surface of the tape member 10. The extended portion 22 of the mesh member 20 may extend at least partially from the edge of the tape member 10, but for example, may also extend from the entire circumference of the edge of the tape member 10. The extended length of the extended portion 22 is preferably 1 mm or more, and may be, as examples, 1~20 mm or 2~15 mm.

As shown in FIG. 8, if the mesh member 20 extends at least partially from the tape member 10, the tape member 10 can be easily peeled off from the mesh member 20 by pressing on the extended portion 22 with a finger.

5. Fifth to Eighth Embodiments

FIG. 9 shows a tape product 100 according to the fifth to eighth embodiments. FIG. 9 shows the tape product 100 as viewed from the base layer 11 side of the tape member 10. FIG. 9 shows an embodiment in which the tape member 10 is easily separated from the mesh member 20 by providing incisions or perforations in the tape member 10.

Figure 9A:
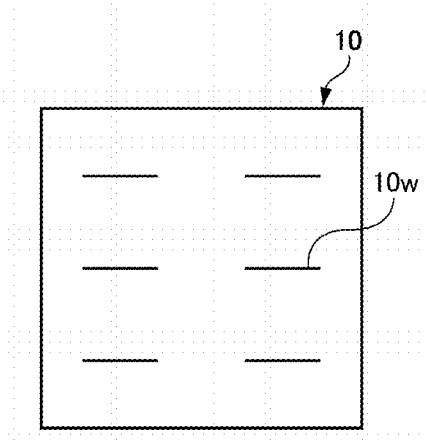
FIG. 9 is a plan view showing an improvement of the tape product.

FIG. 9a shows an example in which one or more linear incisions 10w are formed in the tape member 10 (fifth embodiment). The incisions 10w pass through the tape member 10 in the thickness direction. That is, the incisions 10w are formed in the thickness direction at least across the base layer 11 and the adhesive layer 12. In this example, the incisions 10w do not reach the edge of the tape member 10. By providing these incisions 10w at one or more locations, when peeling the tape member 10 from the mesh member 20, because a finger can be hooked into the incisions 10w, the tape member 10 is able to be easily peeled off from the mesh member 20.

Figure 9B:
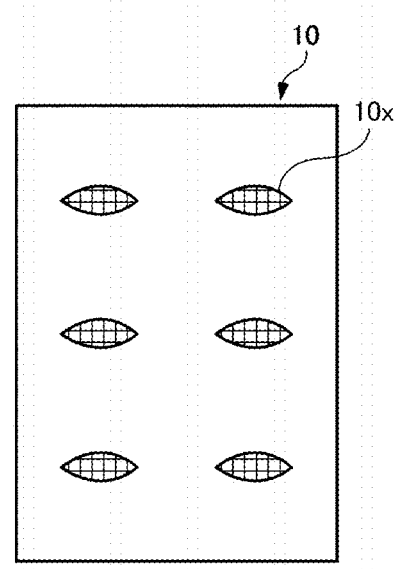

FIG. 9b shows an example in which one or more opened portions 10x are formed in the tape member 10 (sixth embodiment). The opened portions 10x penetrate the tape member 10 in the thickness direction. Therefore, the mesh member 20 on the back side of the tape member 10 can be seen through the opened portions 10x. The shape of the opened portions 10*x* is not particularly limited, and may be, for example, a circular shape, an elliptical shape, a quadrangular shape, or another polygonal shape. By providing these opened portions 10*x* in one or more places, when peeling the tape member 10 from the mesh member 20, because a finger can be hooked into the opened portions 10*x*, the tape member 10 can be easily peeled off from the mesh member 20. In the case where the tape member 10 has stretchability, if the incisions 10*w* as shown in FIG. 9*a* are formed, then by extending the tape member 10 in the direction orthogonal to the extending direction of the incisions 10*w*, the incisions 10*w* will be spread out like the opened portions 10*x* as shown in FIG. 9*b*.

Figure 9C:
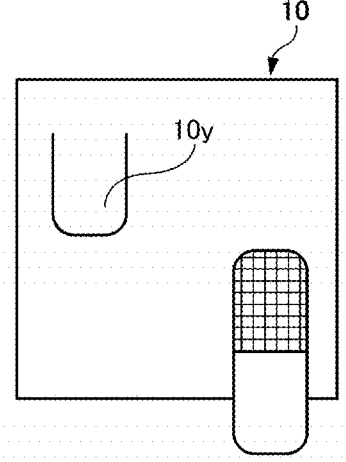

FIG. 9*c* shows an example in which one or more flaps 10*y* are formed on the tape member 10 (seventh embodiment). The flaps 10*y* are portions defined by a fold and a bent or curved incision so as to connect both ends of the fold, and can be folded along the fold. In the example shown in FIG. 9*c*, the flaps 10*y* are formed along one crease and have a U-shaped incision. Thus, by forming the flaps 10*y* on the tape member 10, when peeling the tape member 10 from the mesh member 20, the flaps 10*y* can be raised and held. As a result, if the flaps 10*y* are used, the tape member 10 can be easily peeled off from the mesh member 20.

Figure 9D:
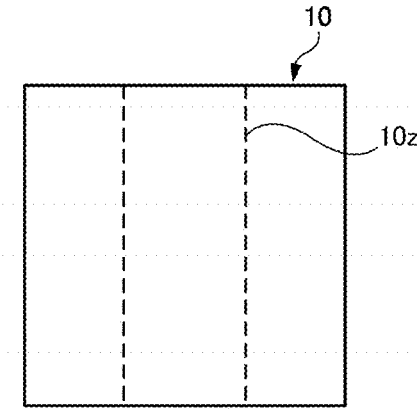

FIG. 9*d* shows an example in which one or more perforations 10*z* are formed in the tape member 10 (eighth embodiment). As shown in FIG. 9*c*, the perforations 10*z* extend from one edge of the tape member 10 to the other edge opposite thereto. The perforations 10*z* penetrate in the thickness direction of the tape member 10. Therefore, a portion of the tape member 10 can be partially peeled along the perforations 10*z*. As described above, by providing the perforations 10*z* so that part of the tape member 10 can be peeled off, the tape member 10 can be easily peeled off from the mesh member 20.

6. Ninth Embodiment

Figure 10A:
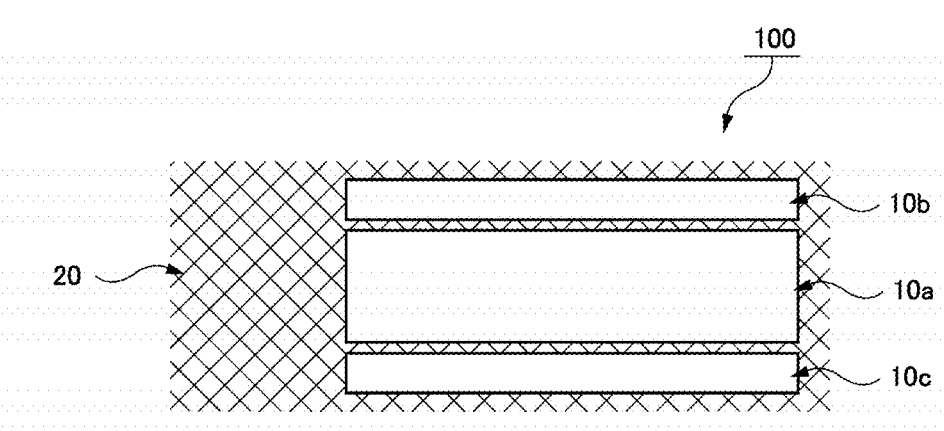
FIG. 10 shows an example in which three separate tape members are provided on the mesh member.
Figure 10B:
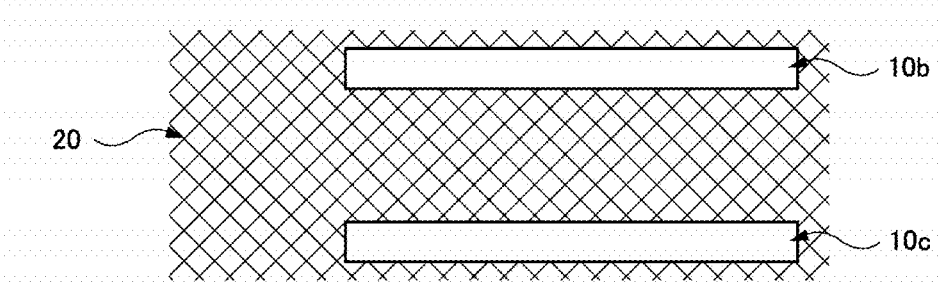
Figure 10C:
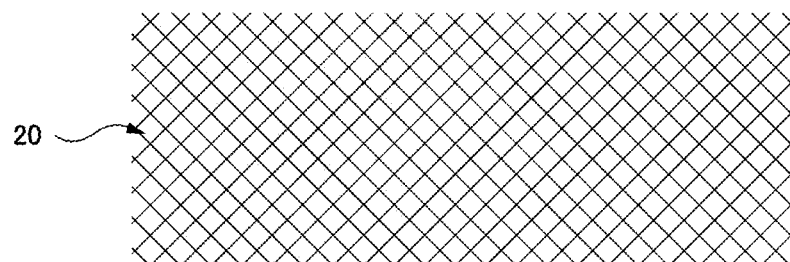

Next, FIG. 10 shows a ninth embodiment of a tape product 100 according to the present invention. As shown in FIG. 9, in the tape product 100 according to the ninth embodiment, a plurality of tape members 10*a*, 10*b* and 10*c* are peelably adhered to a single mesh member 20. That is, slits are formed between the tape members 10*a*, 10*b* and 10*c*, and the tape members 10*a*, 10*b* and 10*c* are separated from each other. From the plurality of tape members, the first tape member 10*a* provided at the center has the largest width, and the second and third tape members 10*b* and 10*c* provided on both sides thereof have a smaller width than the first tape member 10*a*. For example, as shown in FIGS. 10*a*, *b*, and *c*, by doing this, after peeling off the first tape member 10*a* from the skin of a patient, the second and third tape members 10*b* and 10*c* are peeled off in this order, and the peeling operation of each tape member 10*a*, 10*b*, 10*c* is able to be performed. In this way, because gradually peeling off the tape member becomes easier, the risk of wound formation on a patient's skin can be further reduced.

7. Tenth Embodiment

Next, FIG. 11 shows a tenth embodiment of the tape product 100 according to the present invention. In the tape product 100 according to the tenth embodiment, the length in the length direction (horizontal direction in FIG. 10) is longer than the length in the width direction (vertical direction in FIG. 10). This tape product 100 is suitable, for example, for use by winding it around a patient's fingertip or the like. As examples, the length in the length direction of the tape product 100 is preferably 5 times or more or 10 times or more the length in the width direction. An example of the width of the tape product 100 is 10 mm~50 mm.

Further, as shown in FIG. 11, in the tenth embodiment, a first tape member 10*a* and a second tape member 10*b* are provided separately on a single long mesh member 20 by slits. The first and second tape members 10*a* and 10*b* are separated in the width direction, and the length in the longitudinal direction is substantially the same as that of the mesh member 20. That is, the slits separating the first and second tape members 10*a* and 10*b* are formed along the length direction of the mesh member 20.

Figure 11A:
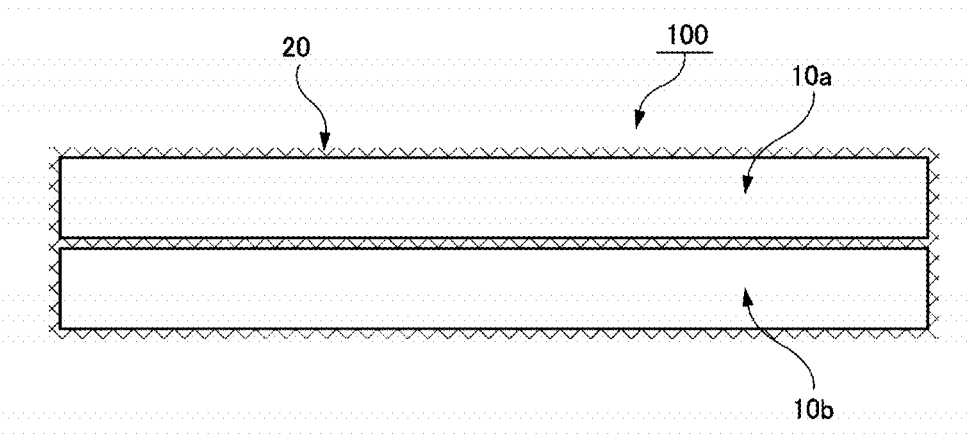
FIG. 11 shows an example in which two separate tape members are provided on the mesh member. In particular.
Figure 11B:
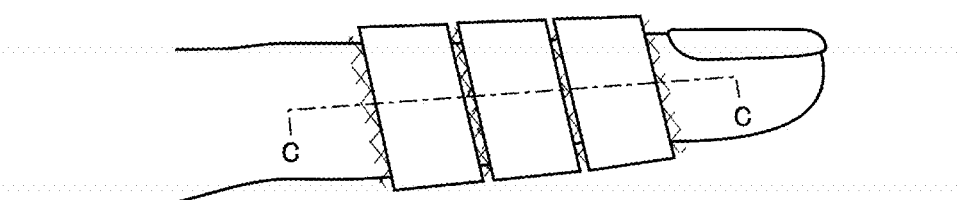
Figure 11C:
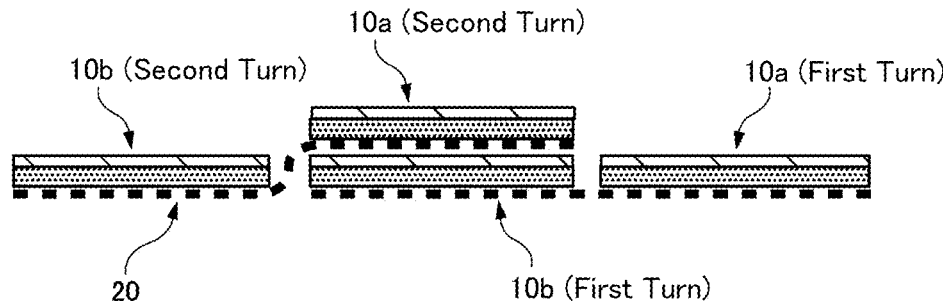

FIGS. 11*b* and 11*c* show an example of how to use the tape product 100 shown in FIG. 11*a*. FIG. 11*c* shows a cross section taken along the line CC shown in FIG. 11*b*. As illustrated, when the tape product 100 is wound around a finger, the first tape member 10*a* in the second turn is preferably overlapped on the second tape member 10*b* in the first turn. In this way, for example, when peeling the second tape member 10*b* from the skin, because the first tape member 10 overlapping on the second tape member 10*b* is twisted, the peeling operation of the tape product 100 is further facilitated. When the tape product 100 is wound around a finger, preventing the first and second turns from overlapping is naturally also possible.

8. Eleventh Embodiment

Figure 12:
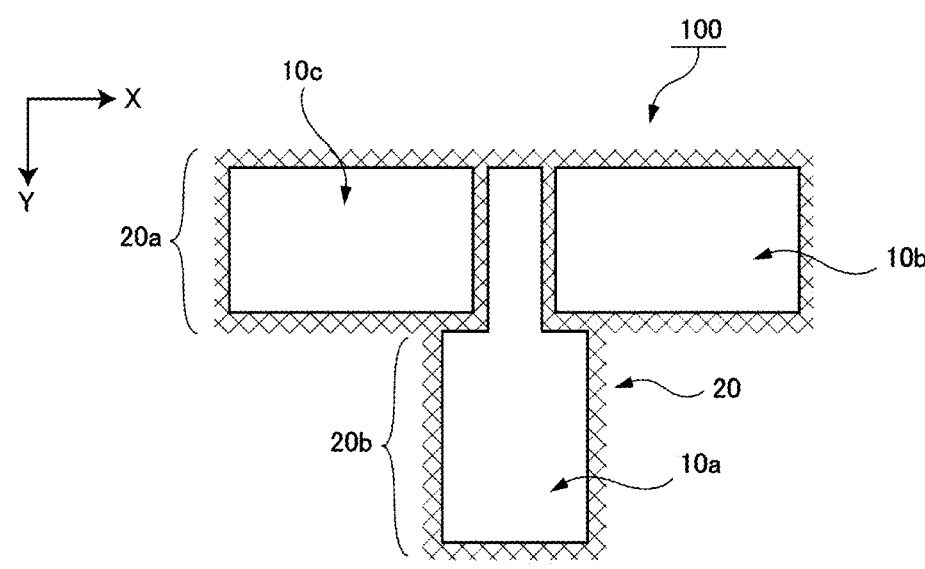
FIG. 12 shows an example in which three separate tape members are provided on the mesh member. In particular.

Next, FIG. 12 shows an eleventh embodiment of a tape product 100 according to the present invention. The tape product 100 according to the eleventh embodiment is formed in a substantially T-shape. The tape product 100 is suitable, for example, for use in covering wounds on a patient's fingertips.

As shown in FIG. 12, in the eleventh embodiment, a single mesh member 20 is formed in a T-shape, and three separate tape members 10*a*, 10*b* and 10*c* are provided thereon so as to be removable. Specifically, the T-shaped mesh member 20 has a first band portion 20*a* extending parallel to the X-axis direction in the orthogonal coordinate system XY in the figure, and the first band portion 20*a* is divided by a second band portion 20*b* extending in parallel with the Y-axis direction from the middle of the first band portion 20*a*. The first tape member 10*a* has a portion disposed on the second band portion 20*b* and an extending section extending from the second band portion 20*b* toward the first band portion 20*a*. The second and third tape members 10*b* and 10*c* are disposed on the first band portion 20*a* on the left and right sides in the X-axis direction of the extended section of the first tape member 10*a*. As described above, if the entire shape of the tape product 100 is T-shaped, it is possible to appropriately cover a wound or the like generated on the fingertip of a patient. Also, by arranging the three tape members 10*a*, 10*b*, and 10*c* separately on the substantially T-shaped mesh member 20, each tape member 10*a*, 10*b*, 10 is able to be easily peeled off from the skin of the wearer.

The present specification has described the embodiments of the present invention with reference to the drawings in order to express the content of the present invention. However, the present invention is not limited to the above embodiments, and includes modifications and improvements apparent to those skilled in the art based on the matters described in the present specification. For example, the embodiments shown in the present specification can be used alone or in combination with other embodiments.

INDUSTRIAL APPLICABILITY

The present invention relates to a tape product that can be used, for example, as a medical tape. Therefore, the present invention can be suitably used in the medical device industry.

The invention claimed is:

1. A tape product comprising:

a plurality of tape members, each having a base layer and an adhesive layer that is laminated on the base layer, in each adhesive layer, an adhesive surface opposite to the base layer is configured to be adhesive to an object; and a mesh member releasably provided on the adhesive surfaces of the plurality of the tape members, wherein a release layer is situated between the plurality of tape members and the mesh member, wherein the adhesive surfaces of the adhesive layers in the plurality of tape members are configured to adhere to the object through openings in the mesh member, wherein the plurality of tape members include a first tape member and a second tape member; and wherein a slit is formed between the first tape member and the second tape member such that the first tape member and the second member is spaced apart by the slit.

2. A tape product comprising:

a first tape member and a second tape member, each having a base layer and an adhesive layer that is laminated on the base layer, in each adhesive layer, an adhesive surface opposite to the base layer is configured to be adhesive to an object; and a mesh member including a release agent on a surface of the mesh member, wherein the adhesive surface of the first tape member and the adhesive surface of the second tape member are releasably provided with the mesh member, wherein a slit where both of the first tape member and the second tape member are not provided is formed with respect to the mesh member such that the first tape member and the second tape member are apart from each other with space in between provided by the slit, wherein the tape product is configured such that (i) when the tape product is attached to the object, the mesh member is disposed between the adhesive surfaces of the first tape member and the second tape member and the object such that the adhesive surface of the first tape member and the adhesive surface of the second tape member adhere to the object through openings in the mesh member in a condition that each adhesive layer is laminated on the base layer, (ii) when the tape product is removed from the object, the adhesive surface of the first tape member is able to be released from the mesh member and the object by peeling off the first tape member from the mesh member using the release agent of the mesh member in a condition that the adhesive surface of the second tape member adheres to the object through openings in the mesh member and that the adhesive layer of the first tape member is laminated on the base layer, (iii) when the tape product is removed from the object, after peeling off the adhesive surface of the first tape member from the mesh member and the object, the adhesive surface of the second tape member is able to be released from the mesh member and the object by peeling off the second tape member from the mesh member using the release agent of the mesh member in a condition that the adhesive surface of the second tape member is laminated on the base layer.

3. The tape product of claim 2, wherein the mesh member comprises at least one coated portion coated with the release agent.

4. The tape product of claim 2, wherein (iv) when the tape product is removed from the object, the surface of the mesh member exposed from the slit is configured to allow at least one finger to be put thereon.

5. The tape product of claim 3, wherein (iv) when the tape product is removed from the object, the surface of the mesh member exposed from the slit is configured to allow a finger to be put thereon.

* * * * *